(12) United States Patent
Reiser et al.

(10) Patent No.: US 10,595,858 B2
(45) Date of Patent: *Mar. 24, 2020

(54) KNOTLESS SUTURE ANCHOR WITH UNTHREADED NOSE

(71) Applicant: DePuy Synthes Products, Inc., Raynham, MA (US)

(72) Inventors: William Reiser, West Jordan, UT (US); Kairi Lofton, McKinney, TX (US); Jeff Parrish, Kaysville, UT (US); Kristian DiMatteo, Waltham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/722,049

(22) Filed: Oct. 2, 2017

(65) Prior Publication Data
US 2018/0021039 A1 Jan. 25, 2018

Related U.S. Application Data

(63) Continuation of application No. 13/220,917, filed on Aug. 30, 2011, now Pat. No. 9,775,605, which is a (Continued)

(51) Int. Cl.
*A61B 17/04* (2006.01)
*A61B 17/86* (2006.01)
*A61B 17/00* (2006.01)

(52) U.S. Cl.
CPC ...... *A61B 17/0485* (2013.01); *A61B 17/0401* (2013.01); *A61B 17/863* (2013.01);
(Continued)

(58) Field of Classification Search
CPC ............ A61B 17/0485; A61B 17/0401; A61B 2017/0496; A61B 2017/0445;
(Continued)

(56) References Cited

U.S. PATENT DOCUMENTS 4,105,034 A 8/1978 Shalaby
4,130,639 A 12/1978 Shalaby
(Continued)

FOREIGN PATENT DOCUMENTS

CN 101321498 12/2008
CN 101422381 5/2009
(Continued)

OTHER PUBLICATIONS

Allcock, Polyphosphazenes, The Encyclopedia of Polymer Science, 1988, vol. 13, pp. 31-41, Wiley Intersciences, John Wiley & Sons.
(Continued)

*Primary Examiner* — Julian W Woo

(57) ABSTRACT

A suture anchor has a tubular body having an axial bore therethrough with one or more purchase enhancements on an exterior surface of the body adapted to enhance purchase of the body within a bone hole. These are preferably screw threads. A distal nose of the suture body has a smooth exterior surface. A length of suture passes down along the exterior surface over the purchase enhancements, over the distal nose, and up into the bore. The smooth exterior surface of the distal nose allows tension of the suture to be held by the engagement of the nose within the bone hole thus making it easier to obtain proper tension as the remaining portion is engaged into the bone hole to provide final fixation.

6 Claims, 21 Drawing Sheets

Related U.S. Application Data continuation-in-part of application No. 12/871,189, filed on Aug. 30, 2010, now Pat. No. 8,460,340.

(52) U.S. Cl.
CPC .............. *A61B 2017/00004* (2013.01); *A61B 2017/044* (2013.01); *A61B 2017/0409* (2013.01); *A61B 2017/0445* (2013.01); *A61B 2017/0451* (2013.01); *A61B 2017/0456* (2013.01); *A61B 2017/0458* (2013.01); *A61B 2017/0496* (2013.01)

(58) Field of Classification Search
CPC .... A61B 2017/0409; A61B 2017/0458; A61B 17/863; A61B 2017/00004; A61B 2017/0456; A61B 2017/044; A61B 2017/0451
See application file for complete search history.

(56) References Cited

U.S. PATENT DOCUMENTS

| | | |
|---|---|---|
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,484,570 A | 11/1984 | Sutter et al. |
| 4,712,681 A | 12/1987 | Branemark et al. |
| 5,037,422 A | 8/1991 | Hayhurst |
| 5,100,417 A | 3/1992 | Cerier |
| 5,152,790 A | 10/1992 | Rosenberg |
| 5,246,441 A | 9/1993 | Ross |
| 5,443,509 A | 8/1995 | Boucher |
| 5,464,929 A | 11/1995 | Bezwada |
| 5,486,197 A | 1/1996 | Le et al. |
| 5,549,633 A | 8/1996 | Evans et al. |
| 5,562,688 A | 10/1996 | Riza |
| 5,595,751 A | 1/1997 | Bezwada |
| 5,597,579 A | 1/1997 | Bezwada |
| 5,607,428 A | 3/1997 | Lin |
| 5,607,687 A | 3/1997 | Bezwada |
| 5,618,552 A | 4/1997 | Bezwada |
| 5,620,698 A | 4/1997 | Bezwada |
| 5,645,850 A | 7/1997 | Bezwada |
| 5,648,088 A | 7/1997 | Bezwada |
| 5,690,676 A | 11/1997 | DiPoto |
| 5,698,213 A | 12/1997 | Jamiolkowski |
| 5,700,583 A | 12/1997 | Jamiolkowski |
| 5,702,397 A | 12/1997 | Globe et al. |
| 5,743,912 A | 4/1998 | Lahille |
| 5,746,752 A | 5/1998 | Burkhart |
| 5,782,862 A | 7/1998 | Bonutti |
| 5,814,051 A | 9/1998 | Wenstrom, Jr. |
| 5,859,150 A | 1/1999 | Jamiolkowski |
| 5,897,574 A | 4/1999 | Bonutti |
| 5,935,129 A | 8/1999 | McDevitt |
| 5,944,739 A | 8/1999 | Zlock |
| 5,957,953 A | 9/1999 | DiPoto |
| 6,013,083 A | 1/2000 | Bennett |
| 6,048,343 A | 4/2000 | Mathis |
| 6,129,730 A | 10/2000 | Bono |
| 6,206,886 B1 | 3/2001 | Bennett |
| 6,234,797 B1 | 5/2001 | Ura |
| 6,290,711 B1 | 9/2001 | Caspari |
| 6,319,252 B1 | 11/2001 | McDevitt |
| 6,436,124 B1 | 8/2002 | Anderson |
| 6,544,281 B2 | 4/2003 | ElAttrache |
| 6,641,597 B2 | 11/2003 | Burkhart |
| 6,660,023 B2 | 12/2003 | McDevitt |
| 6,685,728 B2 | 2/2004 | Sinnott et al. |
| 6,743,233 B1 | 6/2004 | Baldwin |
| 6,752,809 B2 | 6/2004 | Gorek |
| 7,081,126 B2 | 7/2006 | McDevitt |
| 7,083,647 B1 | 8/2006 | Sklar |
| 7,201,754 B2 | 4/2007 | Stewart et al. |
| 7,322,978 B2 | 1/2008 | West, Jr. |
| 7,329,272 B2 | 2/2008 | Burkhart |
| 7,331,982 B1 | 2/2008 | Kaiser |
| 7,449,025 B1 | 11/2008 | O'Donnell |
| 7,517,357 B2 | 4/2009 | Abrams |
| 7,572,275 B2 | 8/2009 | Fallin |
| 7,578,836 B2 | 8/2009 | Justin |
| 7,588,587 B2 | 9/2009 | Barbieri |
| 7,678,134 B2 | 3/2010 | Schmieding |
| 7,682,374 B2 | 3/2010 | Foerster |
| 7,695,494 B2 | 4/2010 | Foerster |
| 7,883,528 B2 | 2/2011 | Grafton |
| 7,993,369 B2 | 8/2011 | Dreyfuss |
| 8,083,769 B2 | 12/2011 | Cauldwell |
| 8,114,128 B2 | 2/2012 | Cauldwell |
| 8,133,258 B2 | 3/2012 | Foerster |
| 8,317,829 B2 | 11/2012 | Foerster |
| 8,409,251 B2 | 4/2013 | Cooper et al. |
| 8,439,946 B2 | 5/2013 | Miller et al. |
| 8,460,340 B2 * | 6/2013 | Sojka ................. A61B 17/0401 606/232 |
| 8,858,596 B2 | 10/2014 | Robison |
| 8,882,801 B2 | 11/2014 | DiMatteo et al. |
| 8,906,060 B2 | 12/2014 | Hart |
| 9,204,872 B2 | 12/2015 | Koepke |
| 9,775,605 B2 * | 10/2017 | Reiser ................ A61B 17/0401 |
| 10,052,091 B2 | 8/2018 | Dreyfuss et al. |
| 2002/0115999 A1 | 8/2002 | McDevitt |
| 2003/0065361 A1 | 4/2003 | Dreyfuss |
| 2003/0120309 A1 | 6/2003 | Colleran et al. |
| 2004/0220573 A1 | 11/2004 | McDevitt |
| 2004/0260345 A1 | 12/2004 | Foerster |
| 2005/0113803 A1 | 5/2005 | Duffy |
| 2005/0283158 A1 | 12/2005 | West |
| 2006/0100630 A1 | 5/2006 | West |
| 2006/0271060 A1 | 11/2006 | Gordon |
| 2006/0276841 A1 | 12/2006 | Barbieri |
| 2007/0005069 A1 | 1/2007 | Contiliano |
| 2007/0010829 A1 | 1/2007 | Nobles |
| 2007/0032792 A1 | 2/2007 | Collin |
| 2007/0060922 A1 | 3/2007 | Dreyfuss |
| 2007/0073299 A1 | 3/2007 | Dreyfuss |
| 2007/0142837 A1 | 6/2007 | Dreyfuss |
| 2007/0142861 A1 | 6/2007 | Burkhart |
| 2007/0173845 A1 | 7/2007 | Kim |
| 2007/0203498 A1 | 8/2007 | Gerber |
| 2007/0213730 A1 | 9/2007 | Martinek |
| 2007/0219557 A1 | 9/2007 | Bourque |
| 2007/0219558 A1 | 9/2007 | Deutsch |
| 2007/0225719 A1 | 9/2007 | Stone |
| 2007/0233122 A1 | 10/2007 | Denis |
| 2007/0270907 A1 | 11/2007 | Stokes et al. |
| 2008/0004659 A1 | 1/2008 | Burkhart |
| 2008/0009904 A1 | 1/2008 | Bourque |
| 2008/0031705 A1 | 2/2008 | Severns |
| 2008/0033460 A1 | 2/2008 | Ziniti |
| 2008/0033486 A1 | 2/2008 | Whittaker |
| 2008/0051836 A1 | 2/2008 | Foerster |
| 2008/0080953 A1 | 4/2008 | Wu |
| 2008/0147063 A1 | 6/2008 | Cauldwell |
| 2008/0147064 A1 | 6/2008 | Cauldwell |
| 2008/0147119 A1 | 6/2008 | Cauldwell |
| 2008/0167660 A1 | 7/2008 | Moreau |
| 2008/0208253 A1 | 8/2008 | Dreyfuss |
| 2008/0215091 A1 | 9/2008 | Dreyfuss |
| 2008/0234730 A1 | 9/2008 | Cotton |
| 2008/0243184 A1 | 10/2008 | Martinek |
| 2008/0249545 A1 | 10/2008 | Shikhman |
| 2008/0255613 A1 | 10/2008 | Kaiser |
| 2008/0262544 A1 | 10/2008 | Burkhart |
| 2008/0269743 A1 | 10/2008 | McNamara |
| 2008/0275431 A1 | 11/2008 | Stone |
| 2008/0275469 A1 | 11/2008 | Fanton |
| 2008/0306511 A1 | 12/2008 | Cooper |
| 2009/0076544 A1 | 3/2009 | DiMatteo |
| 2009/0076545 A1 | 3/2009 | DiMatteo |
| 2009/0082807 A1 | 3/2009 | Miller |
| 2009/0099598 A1 | 4/2009 | McDevitt |

(56) References Cited

U.S. PATENT DOCUMENTS

| | | |
|---|---|---|
| 2009/0149883 A1 | 6/2009 | Brunsvold |
| 2009/0157124 A1 | 6/2009 | Ferragamo |
| 2009/0177229 A1 | 7/2009 | Gulotta |
| 2009/0187216 A1 | 7/2009 | Schmieding |
| 2009/0192546 A1 | 7/2009 | Schmieding |
| 2009/0204147 A1 | 8/2009 | Rahmani |
| 2009/0234387 A1 | 9/2009 | Miller |
| 2009/0248068 A1 | 10/2009 | Lombardo |
| 2009/0281581 A1 | 11/2009 | Berg |
| 2009/0306711 A1 | 12/2009 | Stone |
| 2009/0312794 A1 | 12/2009 | Nason |
| 2009/0318964 A1 | 12/2009 | Lombardo |
| 2009/0326579 A1 | 12/2009 | Anderhub |
| 2010/0004683 A1 | 1/2010 | Hoof |
| 2010/0016869 A1 | 1/2010 | Paulk |
| 2010/0016893 A1 | 1/2010 | Fanton |
| 2010/0049249 A1 | 2/2010 | Lombardo |
| 2010/0069923 A1 | 3/2010 | Nguyen |
| 2010/0069958 A1 | 3/2010 | Sullivan |
| 2010/0121349 A1 | 5/2010 | Meier et al. |
| 2010/0152773 A1 | 6/2010 | Lunn |
| 2010/0179573 A1 | 7/2010 | Levinsohn et al. |
| 2010/0185238 A1 | 7/2010 | Cauldwell |
| 2010/0249835 A1 | 9/2010 | Schwartz |
| 2011/0004243 A1 | 1/2011 | Dreyfuss |
| 2011/0022083 A1 | 1/2011 | DiMatteo |
| 2011/0118762 A1 | 5/2011 | Dooney, Jr. |
| 2011/0264140 A1 | 10/2011 | Lizardi |
| 2011/0276092 A1 | 11/2011 | Dreyfuss |

FOREIGN PATENT DOCUMENTS

| | | |
|---|---|---|
| CN | 101442944 | 5/2009 |
| EP | 1530951 | 5/2005 |
| EP | 1884198 | 2/2008 |
| EP | 1917915 | 5/2008 |
| EP | 2036501 | 3/2009 |
| EP | 2799033 A1 | 11/2014 |
| JP | 2008132327 | 6/2008 |
| JP | 2009101142 | 5/2009 |
| WO | WO 9842261 A1 | 10/1998 |
| WO | WO 0209601 | 2/2002 |
| WO | WO 2006099109 | 9/2006 |

OTHER PUBLICATIONS

Vandorpe et al., Biodegradable Polyphosphazenes for Biomedical Applications, Handbook of Biodegradable Polymers, 1997, pp. 161-182, Hardwood Academic Press.

Kemnitzer et al., Degradable Polymers Derived From the Amino Acid L-Tyrosine, Handbook of Biodegradable Polymers, 1997, pp. 251-272, Hardwood Academic Press.

Heller, Poly(Ortho Esters), Handbook of Biodegradable Polymers, 1997, pp. 99-118, Hardwood Academic Press.

Cohn et al., 1988, Biodegradable PEO/PLA Block Copolymers, Journal of Biomedical Materials Research, vol. 22, pp. 993-1009.

Cohn, New Tailor-Made Biodegradable Polymeric Biomaterials, Polymer Preprints (ACS Division of Polymer Chemistry), 1989, vol. 30, Issue 1, p. 498.

* cited by examiner

KNOTLESS SUTURE ANCHOR WITH UNTHREADED NOSE

RELATED APPLICATIONS

This application is a continuation of U.S. patent application Ser. No. 13/220,917, entitled Knotless Suture Anchor With Unthreaded Nose, filed Aug. 30, 2011, now U.S. Pat. No. 9,775,605 which is a continuation-in-part of U.S. patent application Ser. No. 12/871,189, entitled Knotless Suture Anchor With Unthreaded Nose, filed Aug. 30, 2010, now U.S. Pat. No. 8,460,340 the entire contents of which are hereby incorporated by reference.

BACKGROUND

This application relates to suture anchors and more particularly to knotless suture anchors.

Suture anchors are commonly employed to attach soft tissue such as tendons or ligaments to bone. For instance, in a rotator cuff repair suture is passed through a detached or damaged portion of a rotator cuff tendon. A suture anchor is implanted into the adjacent bone. By attaching the suture to the anchor the tendon is pulled into contact with the bone to promote adhesion of the tendon to the bone.

Such procedures are often performed arthroscopically through a narrow cannula. This reduces trauma to the patient but makes management of suture more difficult. The present invention helps more easily adjust tension on the suture during implantation of a suture anchor.

SUMMARY OF THE INVENTION

A suture anchor according to the present invention comprises a tubular body having an axial bore therethrough. One or more purchase enhancements are provided on an exterior surface of the body and are adapted to enhance purchase of the body within a bone hole. A distal nose of the suture body has a smooth exterior surface. A length of suture passing down along the exterior surface over the one or more purchase enhancements, over the distal nose, and up into the bore. The smooth exterior surface of the distal nose allows tension of the suture to be held by the engagement of the nose within the bone hole thus making it easier to obtain proper tension as the remaining portion is engaged into the bone hole to provide final fixation.

Preferably the one or more purchase enhancements comprise at least one screw thread about the exterior surface. In one aspect of the invention, the distal nose has a diameter equal to a root diameter of the at least one screw thread. In an aspect of the invention the nose has a length of at least one and one half times its diameter.

Preferably, the suture anchor is sterile and formed of a biocompatible material. Also preferably, the body is formed of a bioabsorbable material.

A method according to the present invention provides for affixing tissue to bone. The method comprises the steps of: passing a length of suture through the tissue; passing the length of suture through a suture anchor which comprise a tubular body having an axial bore therethrough, one or more purchase enhancements on an exterior surface of the body adapted to enhance purchase of the body within a bone hole, and a distal nose of the suture body having a smooth exterior surface, the suture passing down along the exterior surface over the one or more purchase enhancements, over the distal nose and up into the bore; tensioning the suture between the tissue and the anchor to a desired tension and placing the distal nose into a bone hole in the bone thereby frictionally engaging the suture between the distal nose and the bone sufficiently to hold the desired tension; and embedding the remainder of the suture anchor into the bone adjacent to the tissue and trapping the suture between the suture anchor body and the bone.

Preferably, the purchase enhancements comprise at least one screw thread and the step of embedding the suture anchor into the bone comprises threading the suture anchor into the bone hole.

Preferably, the step of embedding the suture anchor into the bone is performed while maintaining an essentially fixed length of the suture between the bone hole and the tissue.

Preferably, the bone hole has a diameter less than a diameter of the distal nose. More preferably, the bone hole diameter is at least 10 percent less than the diameter of the distal nose.

DETAILED DESCRIPTION

Figure 1:
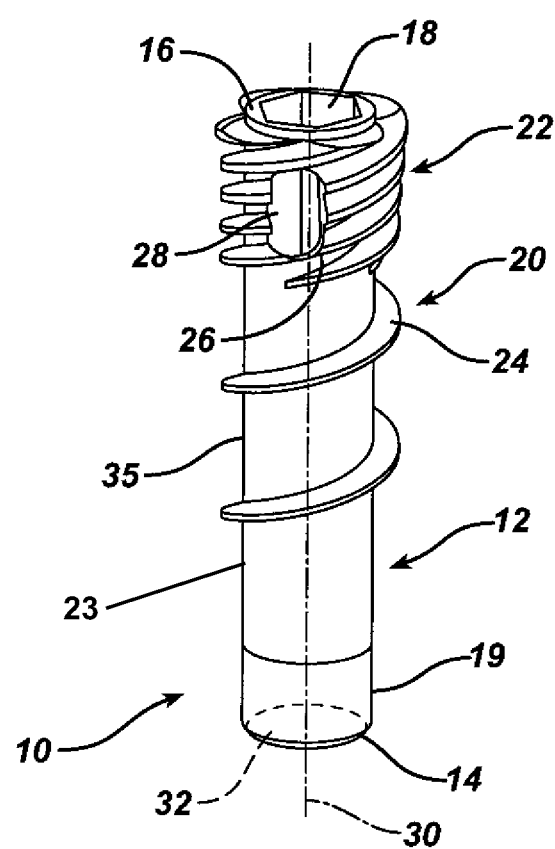
FIG. 1 is a front plan view of a suture anchor according to the present invention.

FIG. 1 depicts a knotless suture anchor 10 according to the present invention. It comprises a body 12 having a distal end 14 and proximal end 16. The proximal end 16 has a hexagonal-shaped tool receiving recess 18. It will be understood to one of skill in the art that alternative tool engagements may be employed. A slight inward taper 19 is provided at the distal end 14 to ease insertion of the anchor 10 into a bone hole (not shown in FIG. 1) and provides an initial fixation of the suture (not shown in FIG. 1) prior to threading the anchor into the hole.

The body 12 has a distal threaded portion 20 and a proximal threaded portion 22 and a distal unthreaded nose 23 distal of the threaded portions 20 and 22. A single exterior thread 24 threads about the body 12 to form the distal threaded section 20. This thread 24 extends nearly to the distal end 14, ending about 0.1 to 0.3 inches short thereof for easier insertion into a bone hole (not shown in FIG. 1). However, one or more additional thread leads 26 begin towards the proximal end 16 to form a multi-fluted threading which distinguishes the proximal threaded portion 22. Each individual thread start 24 and 26 have the same pitch as the thread 24 in the distal threaded section 20, the presence of the one or more additional thread leads 26 provides the proximal threaded portion 22 with an increased effective thread pitch. However, the pitch of each thread lead in the proximal threaded portion 22 remains the same as the pitch of the thread 24 to eliminate axial compression effects from the threads as the anchor 10 is threaded into a bone hole. Preferably, there are four thread leads in the proximal threaded portion 22, the thread 24 and three additional thread leads 26. The major diameter of the proximal threaded portion 22 is preferably somewhat larger than that of the distal threaded portion 20. Rather than have threads with a sharp outer edge the threads 24 and 26 preferably have a rounded our blunted profile to minimize stress on suture that is compressed against them. While the anchor body 12 is shown with threads 24 and 26, especially for smaller diameters, the threads could be replaced with annular flanges or other purchase enhancements appropriate for a push-in anchor versus a threaded anchor. Even with the threads 24 and 26, smaller diameters of the anchor body 12 may be appropriate to push in rather than thread in.

A lateral port 28 passes through the body 12 at an oblique angle to a distally extending longitudinal axis 30 of the body 12 and is disposed within the proximal threaded portion 22. It provides for passage of suture (not shown in FIG. 1) between an inner axial cannulation 32 through the body 12 and an exterior 35 of the body 12. Such function will be explained in detail below.

The body 12 is formed of a suitable biocompatible material and is preferably provided sterile and packaged within a bacteria-proof enclosure (not shown) such that it is ready for a sterile surgical procedure. Many biodegradable materials have less strength and are more brittle than non-biodegradable materials such as PEEK or stainless steel. The simple design of the body 12, without complicated moving or interacting parts, allows easier use of such biodegradable materials while maintaining the structural integrity of the anchor 10.

The novel suture anchors of the present invention may be made from a metallic material, a non-biodegradable polymer, a biodegradable polymer, or a composite of a biodegradable polymer or copolymer and a bioceramic. The term biodegradable as used herein is defined to mean materials that degrade in the body and then are either absorbed into or excreted from the body. The term bioceramic as defined herein is defined to mean ceramic and glass materials that are compatible with body tissue. The bioceramics are preferably biodegradable.

The metallic materials that can be used to manufacture the anchors of the present invention include stainless steel, titanium, alloys of nickel and titanium, or other biocompatible metallic materials.

The non-biodegradable materials that can be used to manufacture the anchors of the present invention include polyethylene, polypropylene, PEEK, or other biocompatible non-absorbable polymers.

The biodegradable polymers that can be used to manufacture the anchors used in the present invention include biodegradable polymers selected from the group consisting of aliphatic polyesters, polyorthoesters, polyanhydrides, polycarbonates, polyurethanes, polyamides and polyalkylene oxides. Preferably, the biodegradable polymers are aliphatic polyester polymers and copolymers, and blends thereof. The aliphatic polyesters are typically synthesized in a ring opening polymerization. Suitable monomers include but are not limited to lactic acid, lactide (including L-, D-, meso and D,L mixtures), glycolic acid, glycolide, .epsilon.-caprolactone, p-dioxanone (1,4-dioxan-2-one), trimethylene carbonate (1,3-dioxan-2-one), .delta.-valerolactone, and combinations thereof.

The bioceramics that can be used in the composite anchors of the present invention include ceramics comprising mono-, di-, tri-, .alpha.-tri-, .beta.-tri-, and tetra-calcium phosphate, hydroxyapatite, calcium sulfates, calcium oxides, calcium carbonates, magnesium calcium phosphates. It is particularly preferred to use a .beta.-tritricalcium phosphate. In addition to bioceramics, bioglasses may also be used in the composite screws. The bioglasses may include phosphate glasses and bioglasses.

Suitable biocompatible synthetic polymers can include polymers selected from the group consisting of aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly (ether urethanes), poly(ester urethanes), polypropylene fumarate), poly(hydroxyalkanoate) and blends thereof.

For the purpose of this invention aliphatic polyesters include, but are not limited to, homopolymers and copolymers of lactide (which includes lactic acid, D-, L- and meso lactide); glycolide (including glycolic acid); .epsilon.-caprolactone; p-dioxanone (1,4-dioxan-2-one); trimethylene carbonate (1,3-dioxan-2-one); alkyl derivatives of trimethylene carbonate; .delta.-valerolactone; .beta.-butyrolactone; .gamma.-butyrolactone; .epsilon.-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; .alpha., .alpha.diethylpropiolactone; ethylene carbonate; ethylene oxalate; 3-methyl-1,4-dioxane-2,5-dione; 3,3-diethyl-1,4-dioxan-2,5-dione-; 6,6-dimethyl-dioxepan-2-one; 6,8-dioxabicycloctane-7-one and polymer blends thereof. Additional exemplary polymer or polymer blends include, by non-limiting example, a polydioxanone, a polyhydroxybutyrate-co-hydroxyvalerate, polyorthocarbonate, a polyaminocarbonate, and a polytrimethylene carbonate. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and E-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al., Hardwood Academic Press, pp. 161-182 (1997). Polyanhydrides include those derived from diacids of the form HOOC—$C_6H_4$—O—($CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in Handbook of Biodegradable Polymers, edited by Domb, et al., Hardwood Academic Press, pp. 99-118 (1997).

Figure 2:
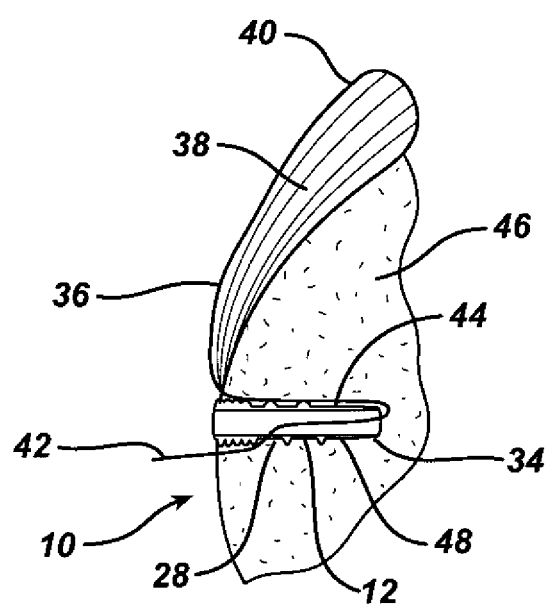
FIG. 2 is a cross-sectional view of the suture anchor of FIG. 1 implanted into a bone.

Turning also to FIG. 2, the suture anchor 10 is shown disposed within a bone hole 34 with a length of suture 36 passing through the anchor body 12 and also through a tendon (such as a tendon in a rotator cuff) 38. A loop 40 of the suture 36 passes through the tendon 38 and its free ends 42 then pass down along a first side 44 of the anchor body 12, being trapped between the anchor body 12, especially by the threads 24 and 26, and bone 46 forming the bone hole 32. The free ends 42 then pass over the distal end 14, into the axial cannulation 32 and then back out of the cannulation 32 through the lateral port 28. From here they pass between a second side 48 of the anchor body 12, being trapped between the body 12 and the bone 46. Other threading arrangements are possible. For instance, rather than passing the loop 40 through the tendon 38 a second anchor, or row of anchors, (not shown) can be placed beneath the tendon 38 with the suture 36 passing from these anchor(s) up through the tendon 38 and to the anchor body 12 or to multiple anchor bodies 12.

Figure 3:
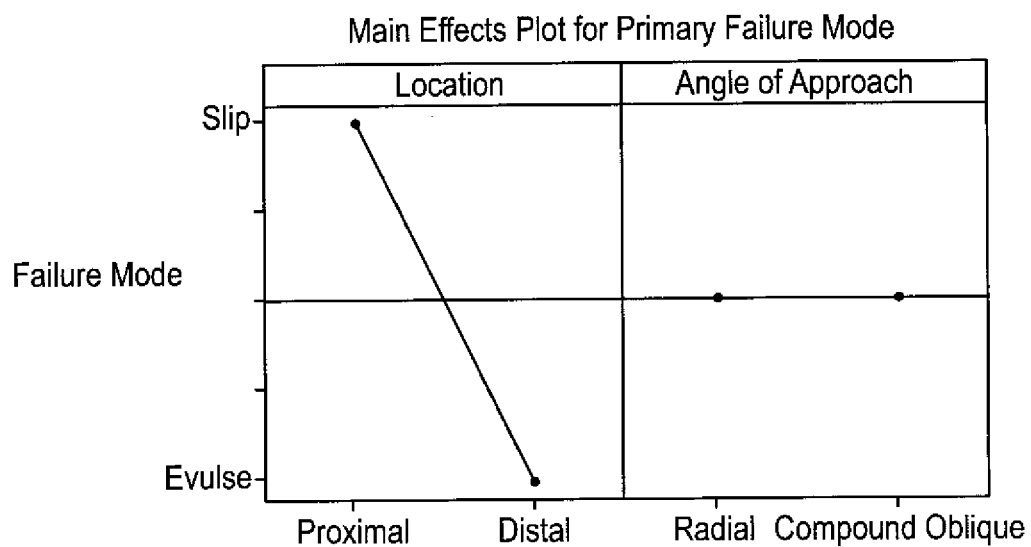
FIG. 3 is a graph of failure modes with respect to the location and angle of a suture passing port of the suture anchor of FIG. 1.
Figure 4:
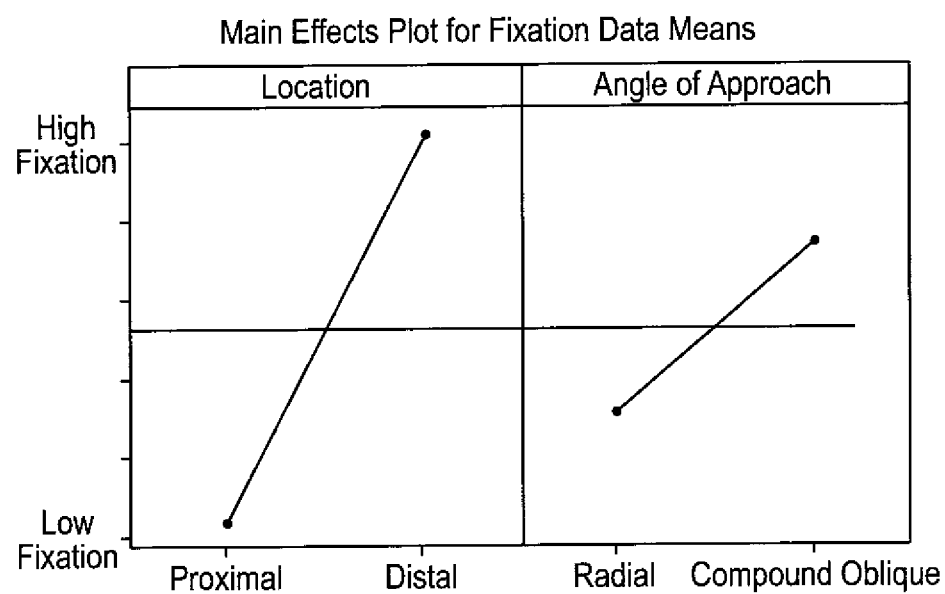
FIG. 4 is a graph of fixation strength with respect to the location and angle of a suture passing port of the suture anchor of FIG. 1.

Turning also to FIGS. 3 and 4, the location of the lateral port 28 affects the strength of the fixation of the anchor body 12 to the bone 46 and also the affixation of the suture 36 to the bone 46 and body 12. A more distal location of the port 28 provides higher fixation strength but the failure mode then tends to be evulsion of the anchor body 12 from the bone hole 34. A failure mode which involves slipping of the suture 36 rather than evulsion of the anchor body 12 is preferred so as to not leave a foreign body free within a patient's joint in an event of failure. Also, an evulsion failure could lead to damage of the bone 46. The angle at which the port 28 passes through the body 12 with respect to the longitudinal axis 30 affects fixation strength with a more oblique angle enhancing fixation.

Additionally, the size and direction which the port 28 passes through the body can affect the functionality and fixation strength of the design. The cross sectional area of the port 28 is provided with sufficient dimension to pass a desired size and quantity of suture(s) through the port 28. The port 28 should not be so small as to damage the suture(s) while transiting the port 28 during loading, deployment or in use. Similarly, passing a disproportionate quantity of suture through an undersized port 28 may result in damage to the anchor body 12 itself. Conversely, the port 28 should not be so large as to minimize the benefit to fixation strength which is derived from the meandering course of suture 36 through the system. An excessively large port size may result in an undesirable degradation of the structural strength of the anchor body. The size of the port may be optimized to provide ease of use and avert damage to the system, while providing benefit within the context of additional fixation strength.

It is favorable to choose the direction of the port 28 as it passes through the body at such angles and locations which promote passage of suture 36 through the system. Obtuse angles formed by the suture 36 during loading and use are most desirable, as they minimize contact friction at corners and subsequently, reduce loading forces and wear and increase robustness of the entire system. The direction of the port 28 may be optimally provided in a compound, oblique direction and offset location with respect to the longitudinal axis. The compound oblique direction and offset location provide an exit of the port 28 which coarsely approximates the tangent of the helices of the thread starts in a distal-to-proximal direction.

This direction and location has been shown to positively affect fixation strength. As the anchor is threaded into a bone hole, it is theorized that the compound oblique direction and offset location of the port 28 promotes a gentle fold of the suture 36 as it exits the port 28, causing the suture 36 to fall easily within the roots between the proximal thread starts. In this context, a port 28 oriented radially normal to the longitudinal axis, for example, would require a sharp fold of the suture 36 as it exits the port 28. The sharp fold thusly presents a sharp transition as the anchor descends into the bone hole past the port 28, thereby weakening the bone by shearing along the wall of the bone hole, ultimately reducing fixation. By not creating sharp bends in the suture 36 it is possible to provide an anchor having smaller dimensions without adding too much additional stress to the suture 36.

Other forms of providing a gentle transition may include the use of a "break edge", fillet or chamfer in the vicinity of the port 28. However, in designs incorporating minimum wall thickness of the anchor, large transition features may result in undesirable increases in the cross sectional area of the port 28.

Figure 5:
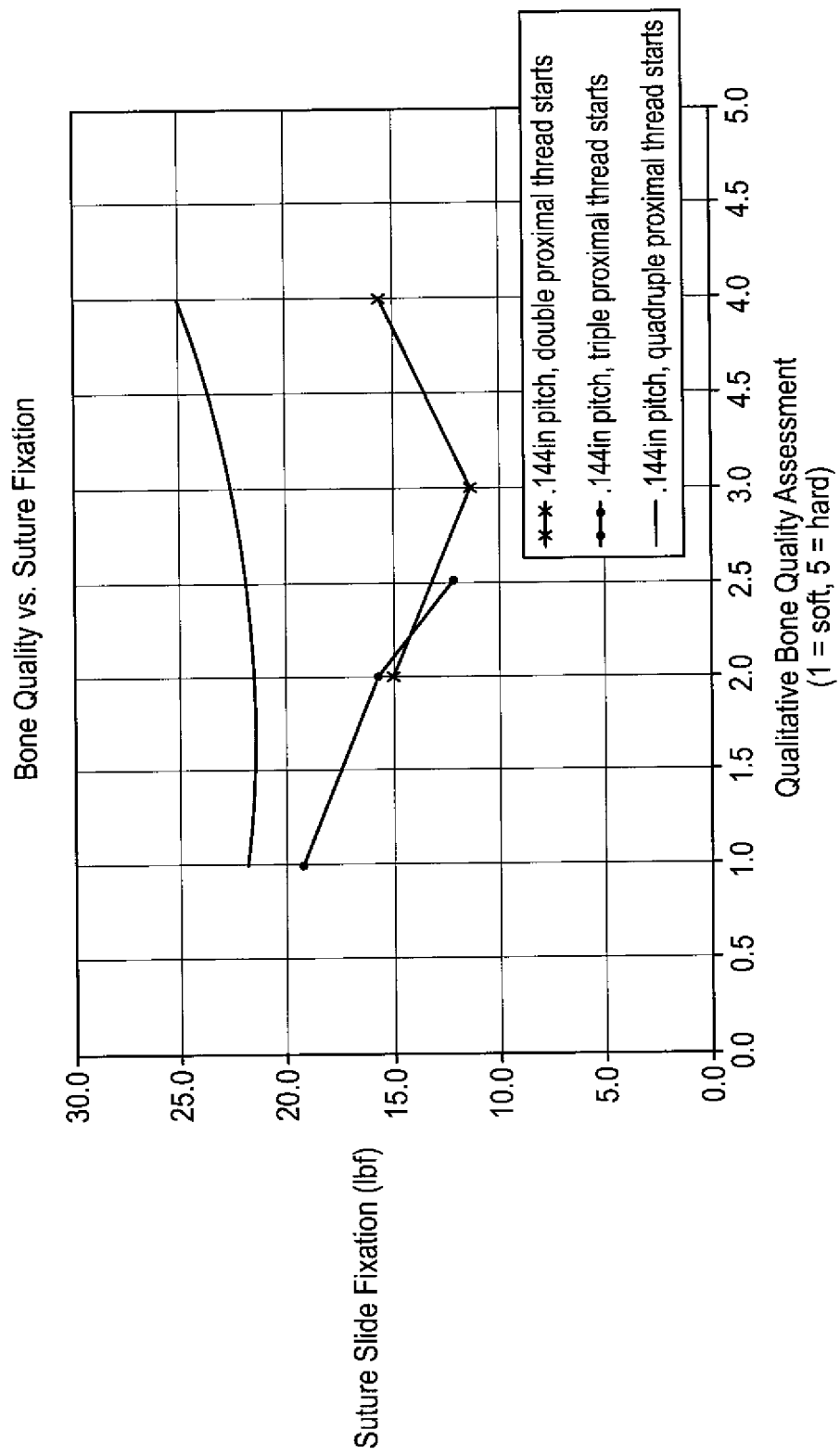
FIG. 5 is a graph of fixation strength versus bone quality for several threading options of the suture anchor of FIG. 1.

Turning also to FIG. 5, one can see that the number of thread leads 26 in the proximal threaded section 22 affects suture 36 fixation between the bone 46 and the anchor body 12. More thread leads enhance such suture 36 fixation. The top line shows optimal fixation with four leads, the thread 24 and three additional thread leads 26.

Ideally, anchor body 12 fixation and suture 36 fixation are optimized to provide maximum anchor body 12 fixation while still providing suture 36 slip as the predominate failure mode over anchor body 12 evulsion.

Figure 6A:
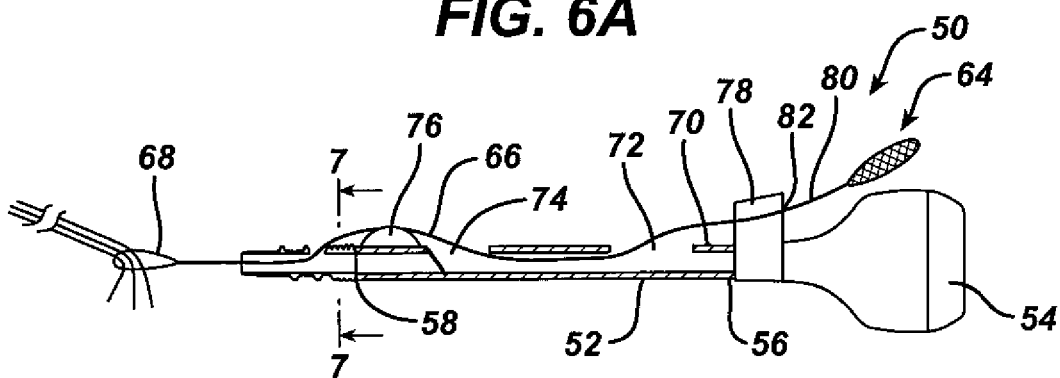
FIGS. 6 A to C are side sectional views of the suture anchor of FIG. 1 and a driver therefor.
Figure 6B:
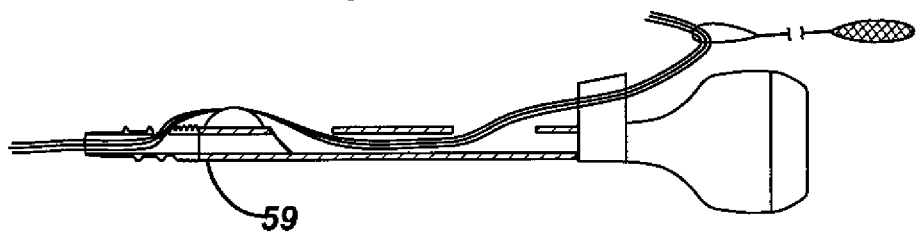
Figure 6C:
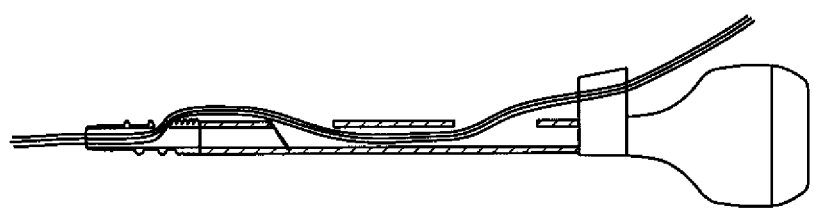
Figure 7:
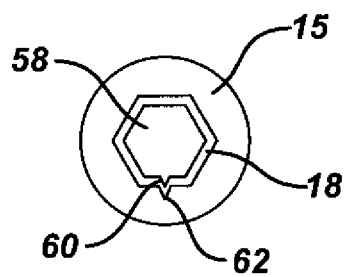
FIG. 7 is a cross-section taken along lines 7-7 of FIG. 6A.

Turning also now to FIGS. 6A, 6B and 6C, the suture anchor body 12 is shown loaded onto an anchor driver 50. The driver comprises an elongated cannula 52 having a driving handle 54 at a proximal portion 56 thereof and a driver tip 58 at a distal portion 59 thereof. The driver tip 58 engages the tool recess 18 on the anchor body 12. Preferably the driver tip 58 is keyed to the anchor body tool recess 18 in such a fashion that the anchor body 12 is placed onto the driver 50 in only one rotational orientation such that a surgeon can determine such orientation by the rotational position of the handle 54. (See FIG. 7 in which a spline 60 on the driver tip 58 fits into a spline receiving cut-out 62 on the anchor body 12.

A suture passer 64, such as the CHIA PERCPASSER (available from DePuy Mitek, Inc., Raynham, Mass.), an elongated braided Nitinol wire 66 with a distal suture grasping loop or kite 68, is engaged to the driver 50 and anchor body 12. It passes into a central lumen 70 of the cannula 52 from a proximal slot 72, out of the lumen 70 from a distal slot 74, over a removable ramp 76 and into the anchor body cannulation 32 through the lateral port 28, with the suture loop 68 extending out of the distal end 14 of the body 12. The wire 66 is flexible but retains some rigidity and the ramp 76 provides a smooth entry angle into the lateral port 28. Preferably, the lumen 70 has an internal ramp where the wire 66 exits at the distal slot 74 in the event it must be re-inserted into the driver 50 after having been removed. A tensioning clutch 78 is interposed between the handle 54 and the cannula 52. A proximal portion 80 of the wire 66 passes through a suture management passage 82 through the clutch 78. During a procedure, after the suture 36 has been passed through the tendon 38, the free ends 42 are pulled out of the procedure cannula (not shown) to a point outside of the patient's body and loaded through the suture loop 68.

After the free ends 42 are loaded into the suture passer 64 it is drawn up the cannula 52 leaving the free ends 42 to pass up through the anchor body cannulation 32 from its distal end 14, out through the lateral port 28, over the ramp 76, into the lumen 70 through the distal slot 72, out of the lumen 70 through the proximal slot 72 and through the clutch suture management passage 82 as depicted in FIG. 6B. The ramp 76 no longer being needed is removed as shown in FIG. 6C. Preferably, the ramp 76 fits to the cannula 52 via a snap-fit to provide easy removal. The anchor is now ready for implantation.

The nose 23 of the anchor body 12 is placed at the hole 34. Preferably, the hole is undersized, preferably about 10 percent, to the diameter of the nose 23. Tension on the suture 36 is adjusted to the desired extent and the nose 23 is pressed into the hole 34. That the nose 23 is unthreaded helps to guide the anchor properly into the hole prior to engaging the threads 20. Frictional engagement between the nose 23 and the bone hole 34 helps to hold the tension as the anchor body 12 is threaded into the hole 34. As the anchor body 12 is threaded into the pre-drilled bone hole 34 via the driver 50. The clutch 78 plays out the free ends 42 as the body 12 approaches and enters the hole 34 to maintain proper tension on the suture 36 and allows the suture 36 to move into the bone hole 34 from the clutch 78 rather than from the tissue and thus avoids spooling of the suture 36 onto the anchor body 12 as it is threaded into the hole 34. The anchor body preferably completes only a partial turn, such as one quarter turn from the time the suture 36 is pinched by the port 28 entering the hole 34 and the anchor body 12 is fully seated therein. The anchor body 12, especially in its interior, and the suture 36 can be formed of materials or have their surfaces enhanced with materials or procedures which lower friction and enhance slipping of the suture 36 as the anchor is deployed. When fully deployed the proximal end 22 of the anchor body 12 is preferably below the bone 46 within the bone hole 34. The driver 50 is removed and the free ends 42 trimmed leaving the anchor 10 in place as shown in FIG. 2.

Figure 8:
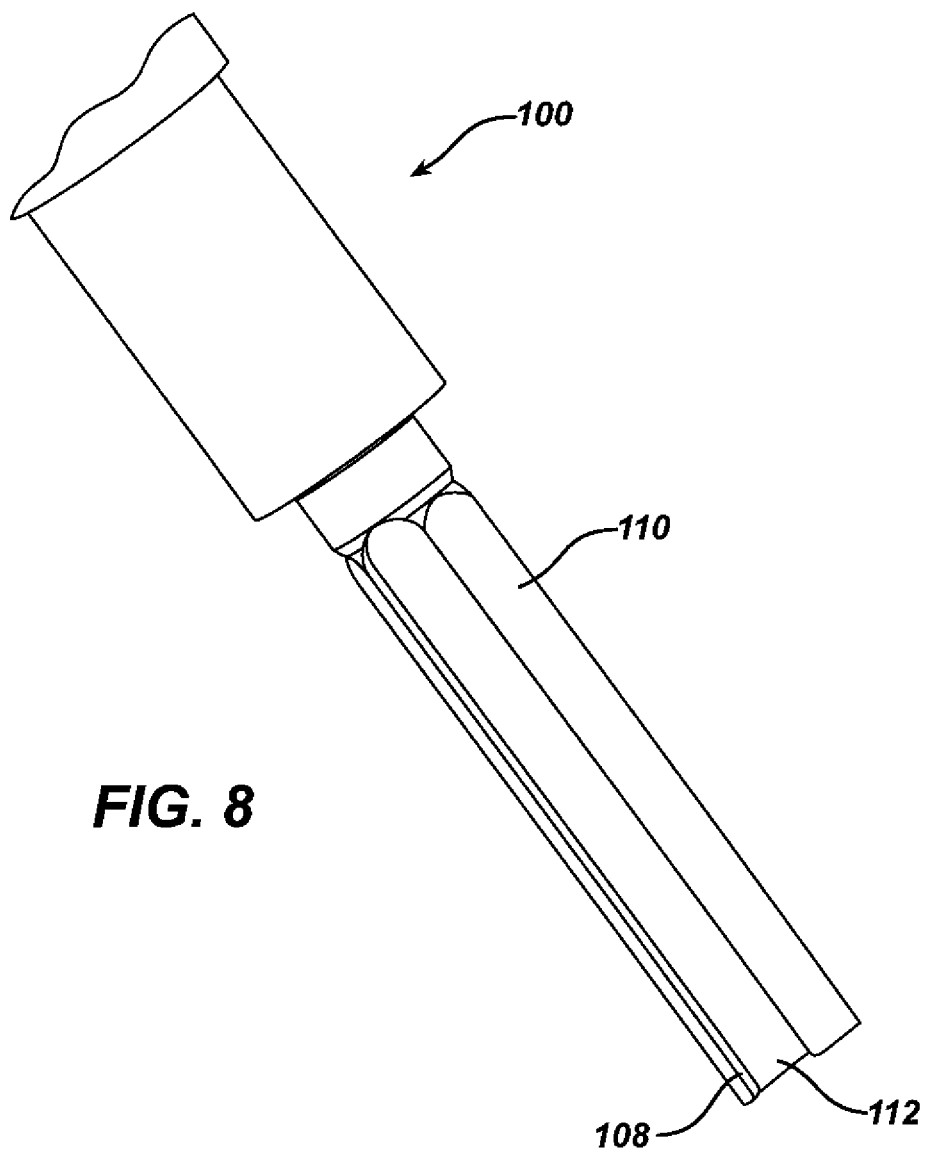
FIG. 8 is a perspective view of an alternate driver head according to the present invention.
Figure 9:
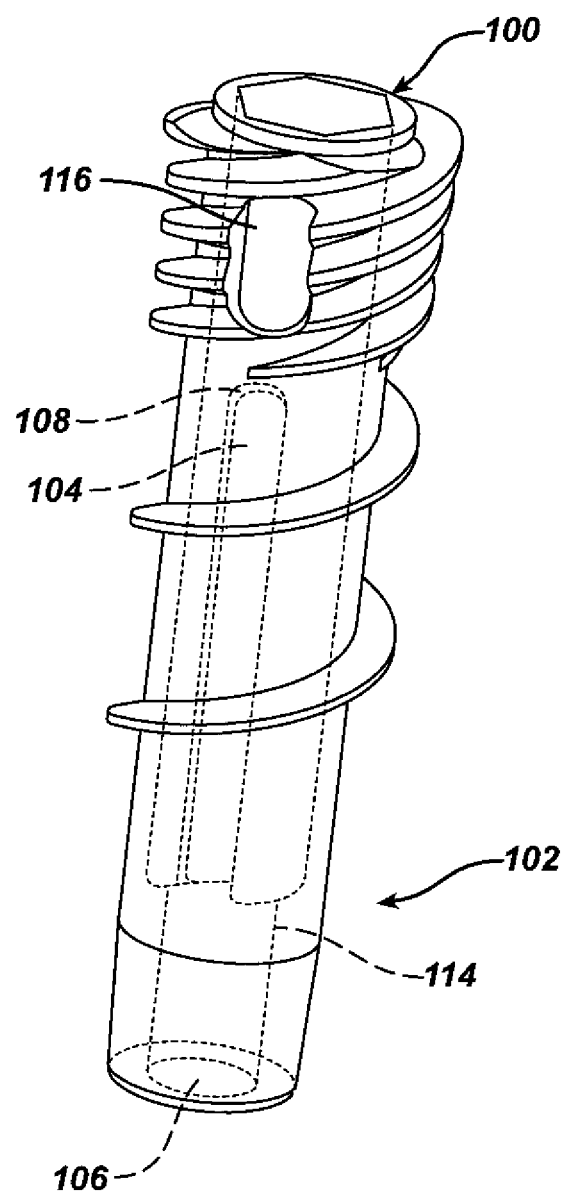
FIG. 9 is a wire drawing in perspective of the driver head of FIG. 8 received within a further embodiment of a suture anchor according to the present invention.

FIG. 8 illustrates an alternative embodiment of an insertion tool 100 and FIG. 9 illustrates an alternative embodiment of an anchor 102 according to the present invention, each of these being adapted for use together. The anchor 102 has a structure similar to the anchor 10 with the exception of an axial boss 104 within its axial cannulation 106 which mates with a distal axial slot 108 in a distal driving portion 110 of the insertion tool 100. Also, the axial cannulation 106 is enlarged radially where the driving portion 110 is received such that an interior cannulation 112 of the driving portion 110 has the same interior diameter as a distal portion 114 the anchor axial cannulation 106 and the boss 104 extends radially into the slot 108 to a depth matching the interior diameter of the interior cannulation 112, providing a smooth transition within the of the interior cannulation 112 and axial cannulation 106 eliminating discontinuities upon which suture can snag during rotational deployment of the anchor 102. The boss 104 provides additional engagement between the insertion tool 100 and the anchor 102. To enhance rigidity the inner cannulation 112 can be formed with its distal portion as shown in FIG. 8, a large axial bore, but with its proximal portion being no wider than the slot 108, preferably all with smooth transitions.

Figure 10:
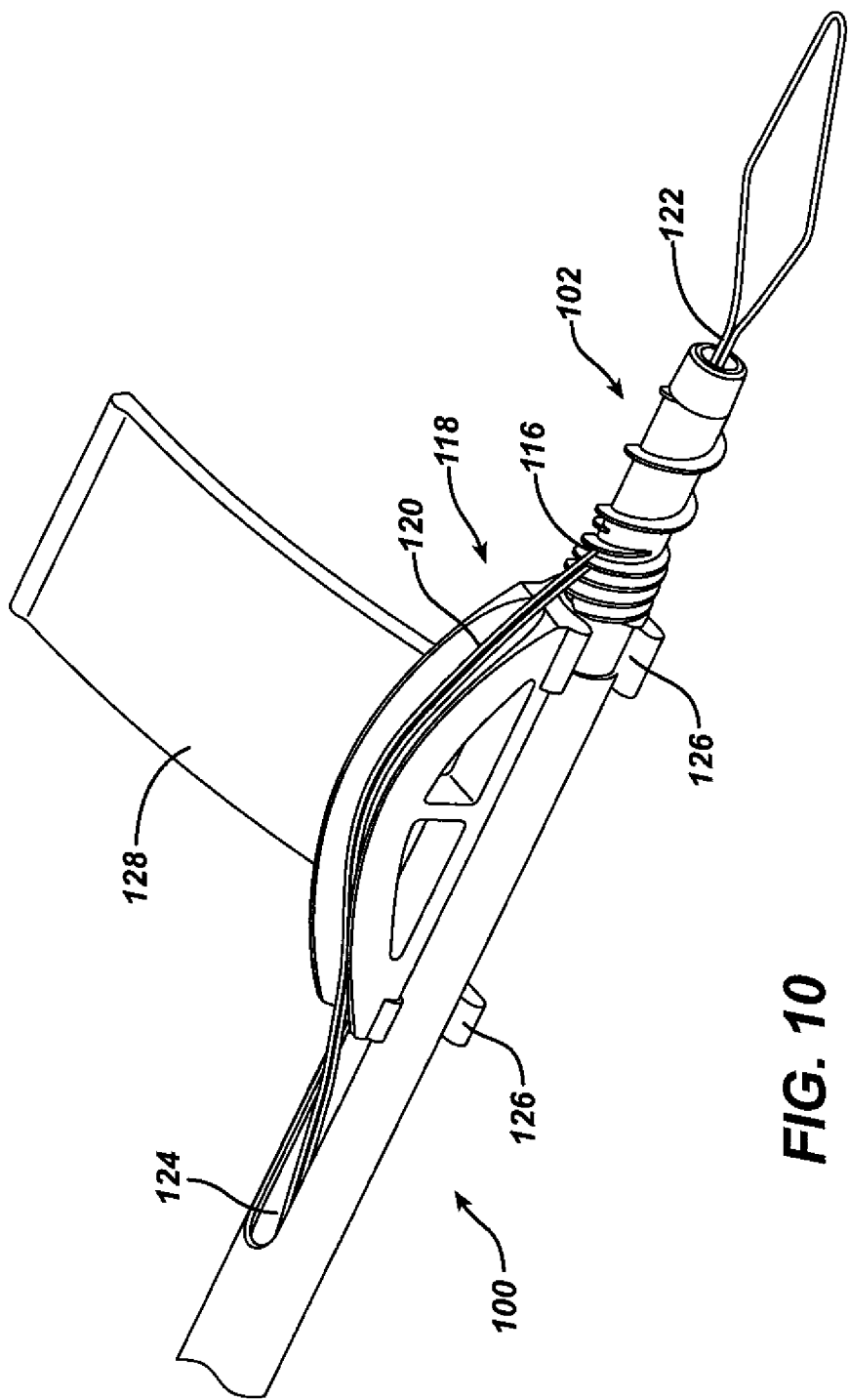
FIG. 10 is a close-up perspective view of the driver and suture anchor of FIG. 9.
Figure 11:
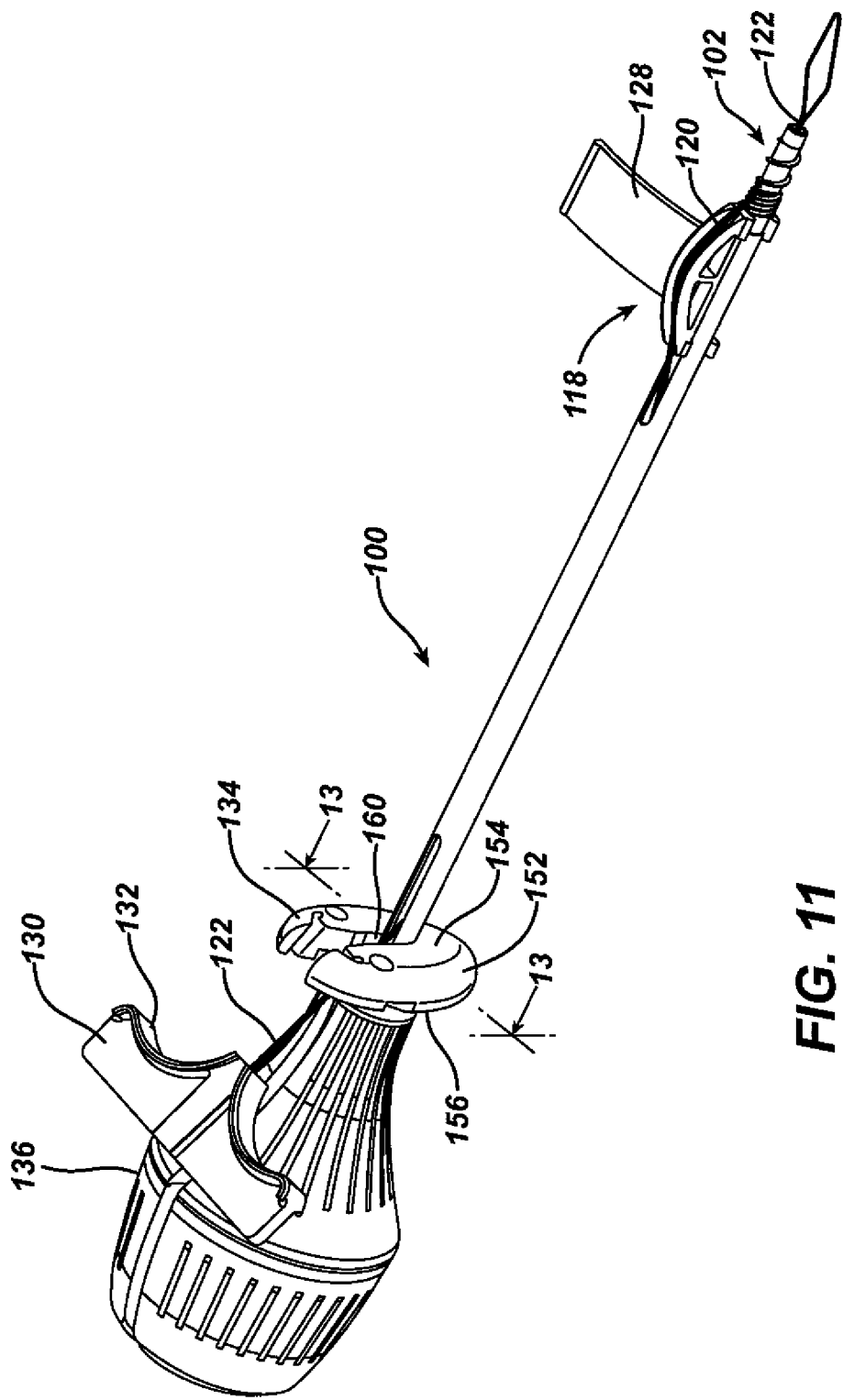
FIG. 11 is a perspective view of the driver and suture anchor of FIG. 9.

Turning also to FIGS. 10 and 11, the boss 104 aligns circumferentially with a lateral port 116 on the anchor. A suture ramp 118 aligns on the insertion tool 100 with the port 116. The alignment of the boss 104 with respect to the port 116 and the slot 108 with respect to the ramp 118 puts the port 116 and ramp 118 into circumferential alignment with one another.

The ramp 118 is formed of a molded polymer having an arcuate suture receiving groove 120 which extends radially outwardly to guide suture and/or a suture grasper 122 out of a slot 124 on the insertion tool 100 and into the port 116 without sharp transitions and with the suture or suture grasper 122 forming an oblique angle with respect to itself as it enters the port 116. The ramp 118 also bears a pair of C-shaped snap clips 126 which snap onto and off of the insertion tool 100 for easy removal of the ramp 118 during the procedure previously described. A grasping tab 128 provides a gripping surface for easy manual removal of the ramp 118 and also provides a surface upon which to place instructions for use.

As shown in FIG. 11 a T-shaped handle 130 on the suture grasper 122 preferably has finger lands 132 for easy manipulation of the suture grasper 122. A suture clutch 134 which normally holds the suture and then releases it as torque is provided to a handle 136 on the insertion tool 100 is shown distal of the handle 136 but could be incorporated therein. Details on preferred clutch mechanisms are provided later herein.

Figure 12:
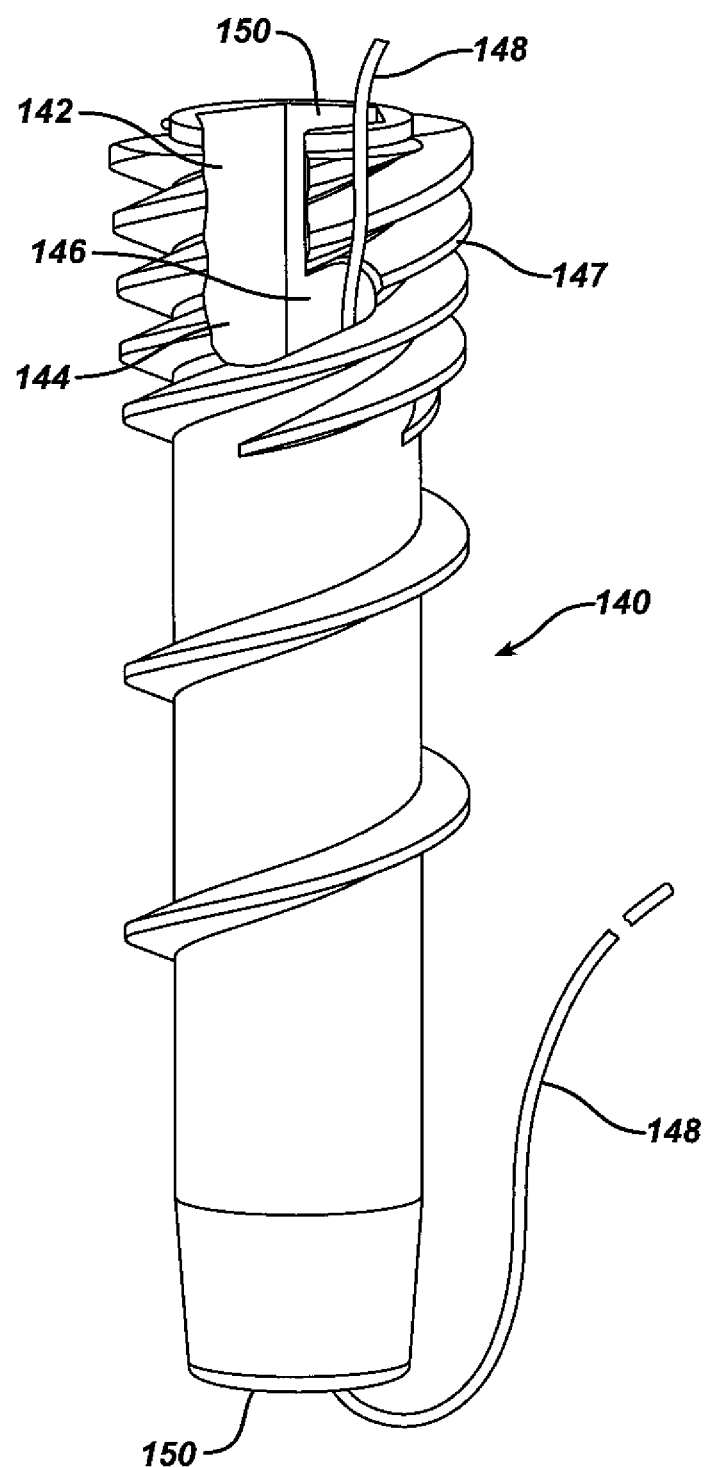
FIG. 12 is a front plan view of a further embodiment of a suture anchor according to the present invention.

FIG. 12 illustrates a further embodiment of a suture anchor 140 according to the present invention. It is similar to the prior suture anchors 10 and 102; however, instead of a port it carries an axial slot 142 at its proximal end. The slot 142 terminates at its distal end 144 with a return portion 146 which extends proximally and circumferentially along a path of a thread start 147 providing an overall hook shape to the slot 142. Being open at its proximal end allows for easier threading of a suture grasper (not shown in FIG. 12).

Ease of threading is so improved that the grasper can be omitted in which case during the procedure a surgeon can directly thread a suture 148 through a main axial cannulation 150 of the anchor 140, feeding it into the slot 142 and seating it within the slot return portion 146. A procedure with the anchor 140 would proceed as previously described with the surgeon pre-drilling a hole in a bone and passing suture 148 through tissue, preferably in an arthroscopic procedure through a cannula (the cannula, tissue and bone not being shown in FIG. 12). With free ends of the suture 148 outside of the patient's body the surgeon passes them through the cannulation 150 and seats the suture within the return portion 146. The anchor 140 would then be loaded onto an insertion tool such as the tool 100 or 50 and installed into the bone as previously described, the return portion 146 holding the suture similarly to the aforementioned ports. Preferably the return portion passes into the cannulation 150 at an oblique angle as described with respect to the prior ports thus allowing the suture 148 to pass into the cannulation 150 through the return portion 146 while keeping an oblique angle with respect to itself.

Figure 13:
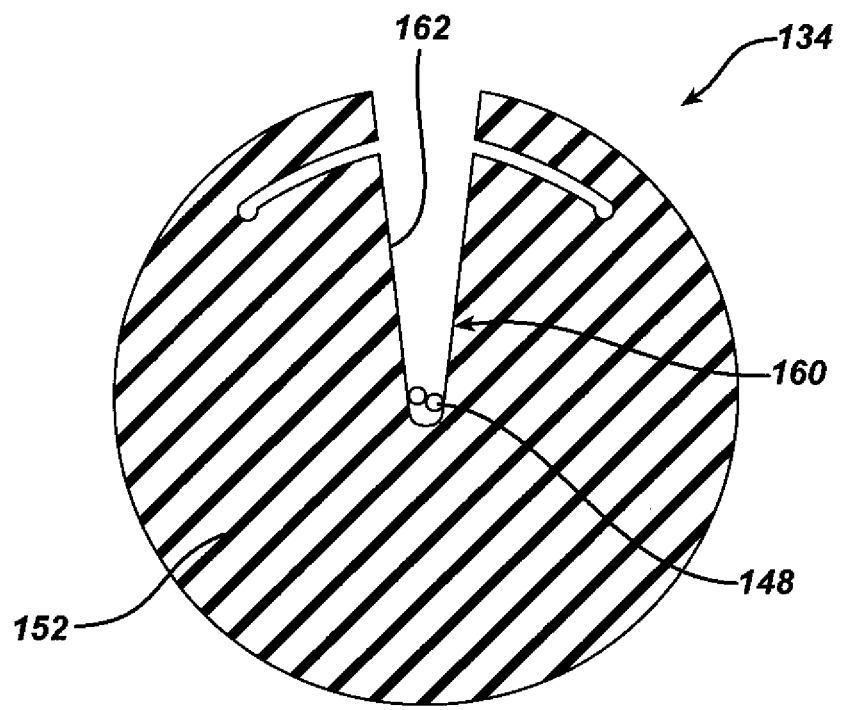
FIG. 13 is a sectional view taken along lines 13-13 of FIG. 11.

The clutch 134 comprises a disk shaped body 152 having a distal portion 154 which attaches to an elongated cannula 156 which itself terminates in the hexagonal driving portion 110. A proximal portion 158 of the body 152 attaches to the insertion tool handle 136 outwardly radially of where the cannula 156 attaches to the body 152. An axial slot 160, as best seen in FIG. 13, leads into the body 152 and receives and grabs the suture 148. Preferably its interior surface 162 is formed of a rubber or other resilient material to enhance the grip with the suture 148. Torque applied to the handle 136 is transmitted through the clutch body 152 to the cannula 156. The body 152 is formed of a material, such as a hard rubber, having sufficient resilience to allow the slot 160 to open under the influence of such torque and relax the grip on the suture 148. Thus, the clutch 134 normally grips the suture to maintain tension but relaxes that grip as the handle 136 is torqued during implantation of the anchor 140 allowing suture 148 to slide through the clutch 134.

Figure 14:
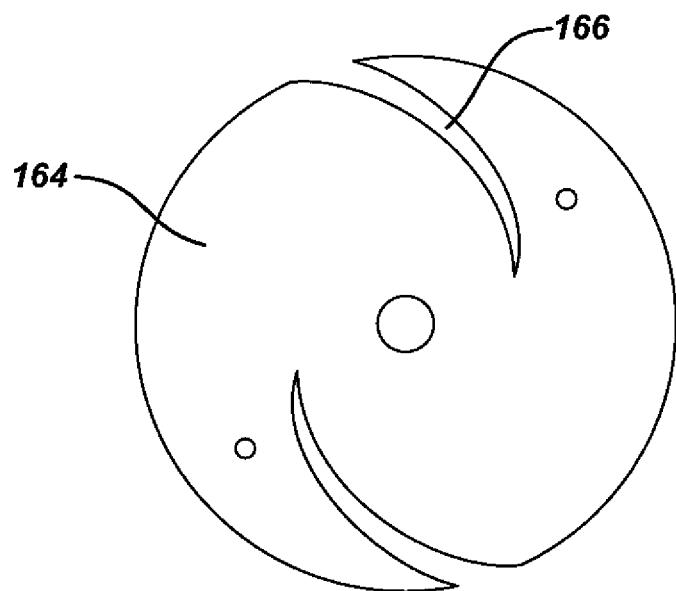
FIG. 14 is an end view of a further embodiment of a suture retaining clutch according to the present invention.

FIG. 14 illustrates an alternate embodiment of a clutch body 164 according to the present invention. It comprises a pair of somewhat radial slots 166 which spiral inwardly radially in a direction in which torque would be applied to an associated handle (not shown in FIG. 14).

Figure 15:
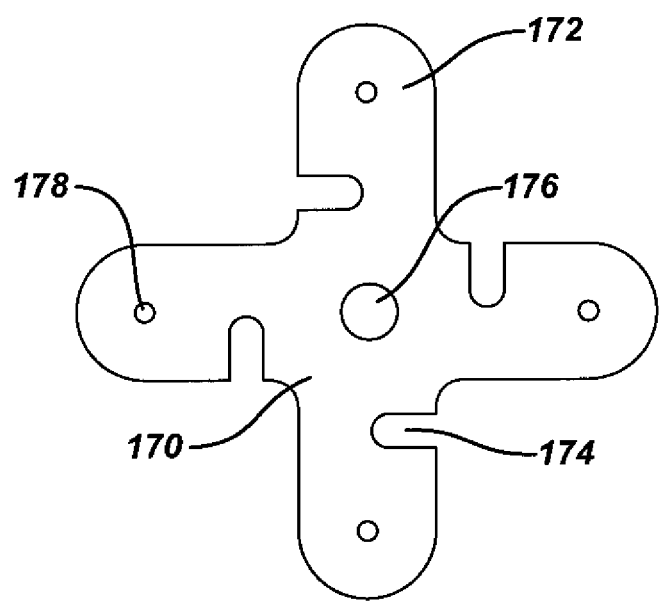
FIG. 15 is an end view of a further embodiment of a suture retaining clutch according to the present invention.

FIG. 15 illustrates a further embodiment of a clutch body 170 comprising a plurality of radially extending arms 172, each having circumferential suture receiving slots 174 therein. A cannula attachment location 176 is located in the center of the body 170 and handle attachment locations 178 are located on the arms outwardly radially of the slots 174.

Figure 16A:
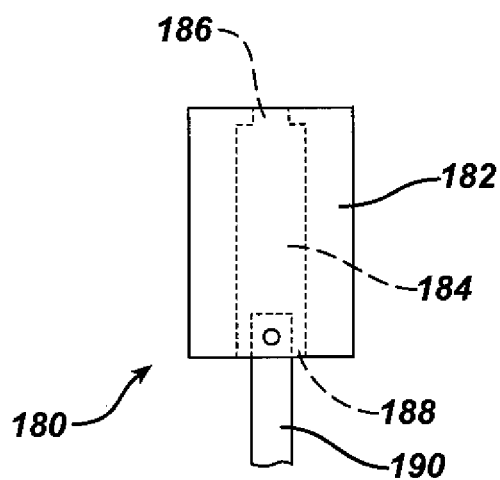
FIG. 16A is a front elevation view of a further embodiment of a suture retaining clutch according to the present invention.
Figure 16B:
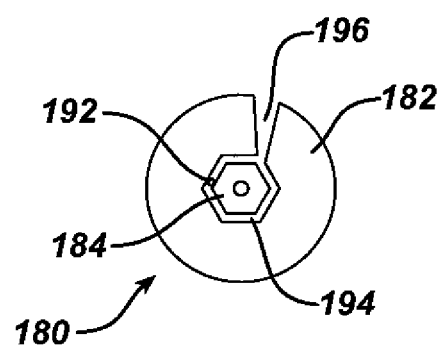
FIG. 16B is an end view from a distal end of the suture retaining clutch of FIG. 16A.

FIGS. 16 A and B illustrate a further embodiment of a clutch mechanism 180 which comprises a rigid outer handle gripping portion 182 and a radially interior resilient insert 184. A proximal end 186 of the insert 184 attaches to the outer handle 182 and a distal end 188 of the insert 184 attaches to a cannula 190. Suture 192 feeds into a gap 194 between the outer handle 182 and the insert 184 through a radial slot 196 in the handle 182. The gap 194 is sized to grip the suture 192. Application of torque to the outer handle 182 twists the insert 184 thereby opening the gap 194 and allowing slippage of the suture 192 therethrough.

Figure 17A:
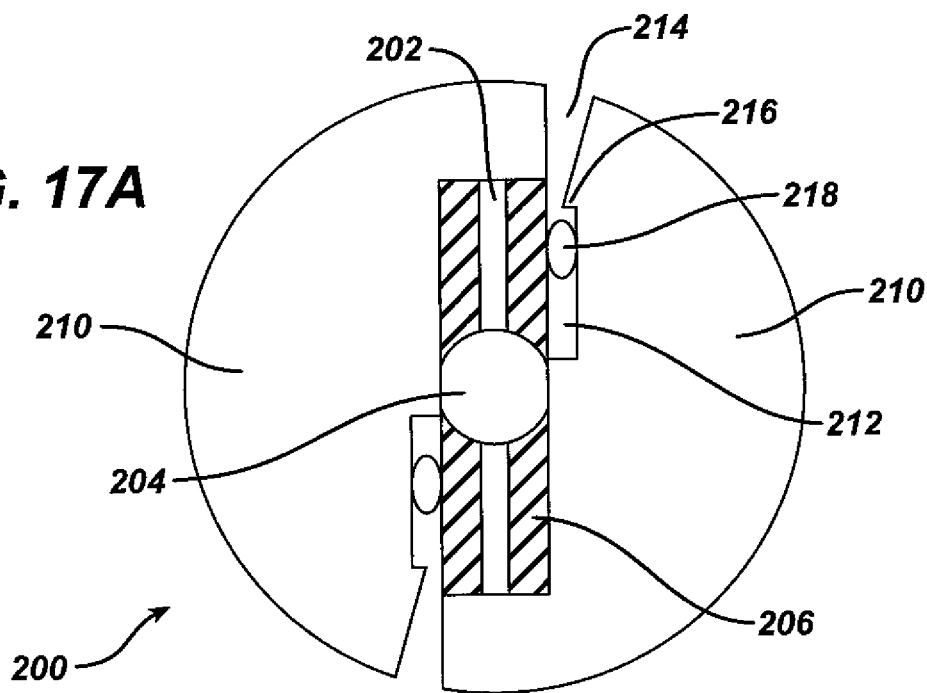
FIGS. 17 A and B are sectional views of a further embodiment of a suture retaining clutch according to the present invention.
Figure 17B:
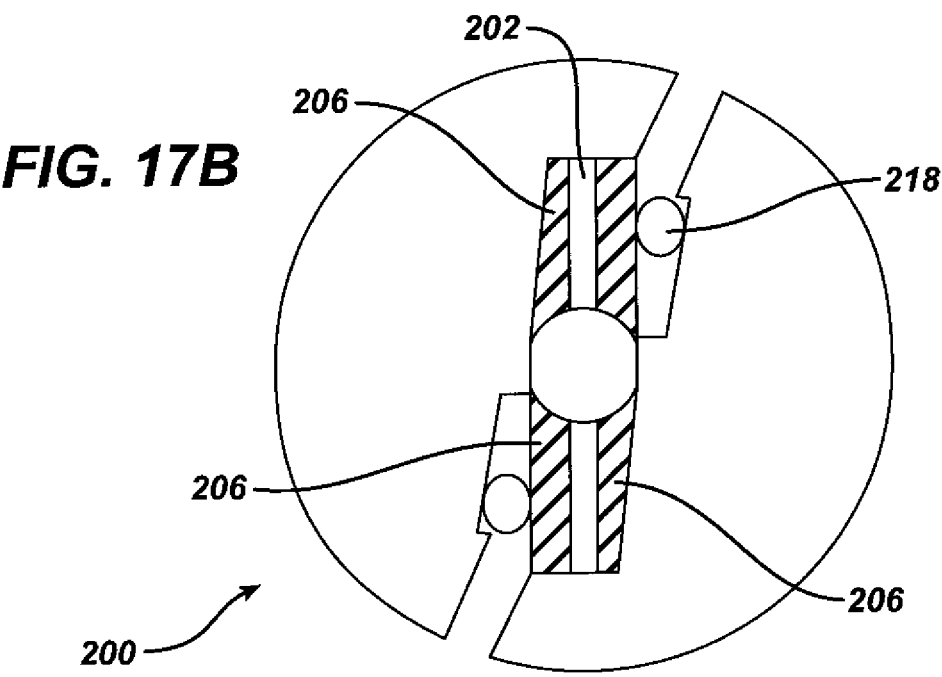

FIGS. 17 A and B illustrate a further embodiment of a clutch mechanism 200 comprising a pair of radial flanges 202 extending outwardly radially from a cannula proximal portion 204. A resilient material 206 such as rubber affixes to both sides of the flanges 202. An outer handle 208 comprises two halves 210, each of which attach to one of the flanges 202 and which are spaced apart from the opposing flange 202 to create suture receiving slots 212. The slots 212 can have flared openings 214 with a suture retaining lip 216 therein. Suture 218 is gripped within the slots 212 by compression between the outer handle 208 and the resilient material 206 on the flange 202 as shown in FIG. 17 A. Application of torque to the outer handle 208 compresses the resilient material between the handle 208 and flanges 202 to open the slots 212 to release the suture as shown in FIG. 17 B.

Figure 18A:
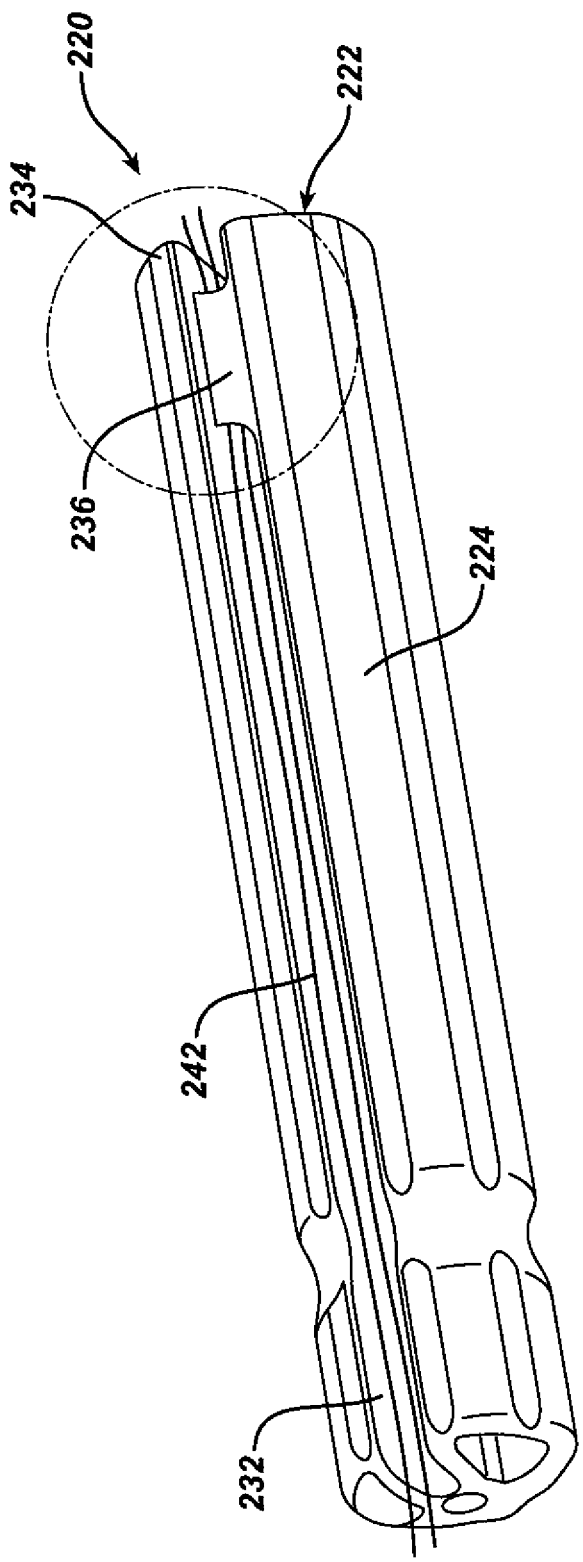
FIG. 18A is a perspective view of a suture driver handle embodying a further embodiment of a suture retaining clutch according to the present invention.
Figure 18B:
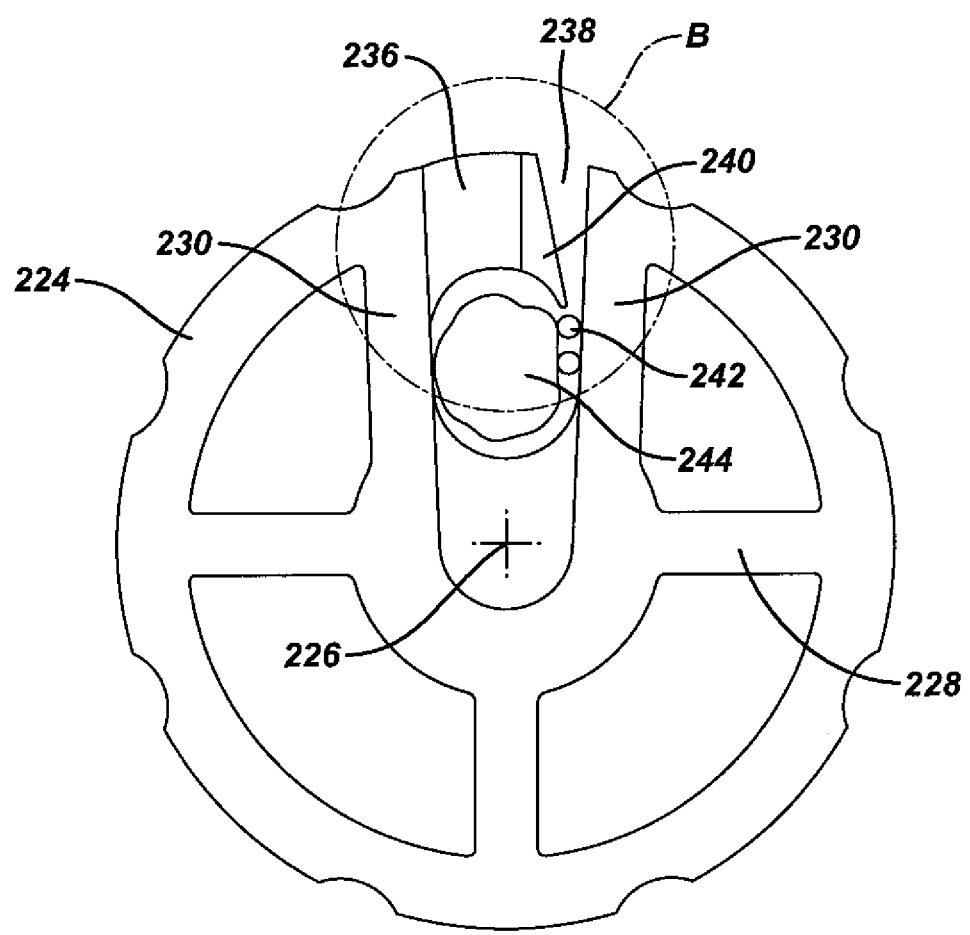
FIG. 18B is an end view from a proximal end of the suture driver handle of FIG. 18A.

FIGS. 18 A and B illustrate an additional embodiment of a clutch mechanism 220. A handle 222 comprise an outer cylindrical gripping portion 224 and a central axial core 226, the gripping portion 224 being attached to the core 226 via a plurality of radial ribs 228. One pair of ribs 230 extend slightly off axis and adjacent to each other and the gripping portion 224 is open between them forming a radially extending axial slot 232 in the handle 222. Near a proximal end 234 of the handle 222 a retainer member 236 sits within the slot 232 extending from one of the ribs 230 toward the adjacent rib 230. It has a flared opening 238 and a retaining lip 240 to ease entry of suture 242 into the slot 232 with the lip 240 holding it from falling out. A resilient material 244 in the slot 232 grips the suture 242. Torque applied to the gripping portion 224 tends to open the slot 232 releasing the tension on the suture 242.

Figure 19:
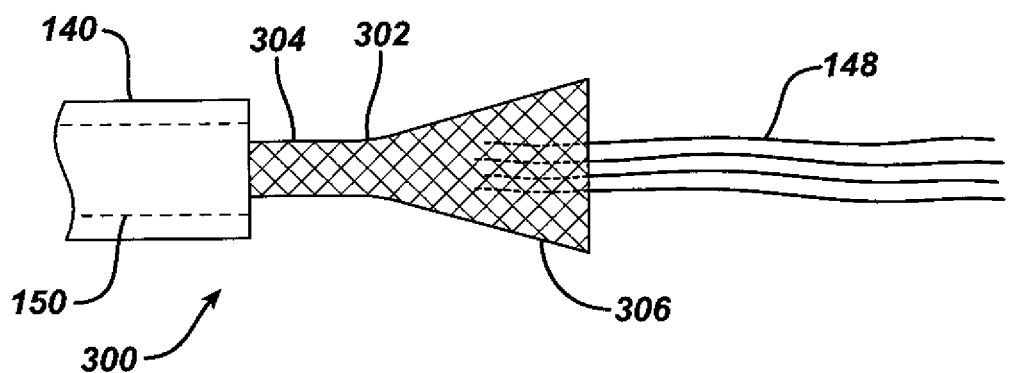
FIG. 19 is a side elevation view of a suture threader according to the present invention.

Threading the suture 148 through the cannulation 150 of the suture anchor 140 of FIG. 12 can be accomplished manually without assistance from a threading device. However, a simple converging threader 300 as illustrated in FIG. 19 can further simplify the procedure. The threader 300 comprises an open braided tube 302 having one end 304 inserted through the cannulation 150 and a second expanded end 306 into which one or more sutures 148 can be pushed by hand. The threader 300 is preferably woven from a flexible biocompatible material and provided in combination with the anchor 140, with the threader 300 received through the cannulation 150, and with both the threader 300 and anchor being sterile and packaged within a sterile bacteria-proof package (not shown). When a surgeon is ready to load sutures 148 into the anchor 140 the combination of the anchor 140 and threader 300 are removed from the sterile package and the sutures 148 are pushed into the threader expanded end 306. Tension is applied to the other end 304 causing the expanded end 306 to close and travel through the cannulation 150 carrying the sutures 148 therethrough. The procedure can then be completed as aforementioned.

Figure 20:
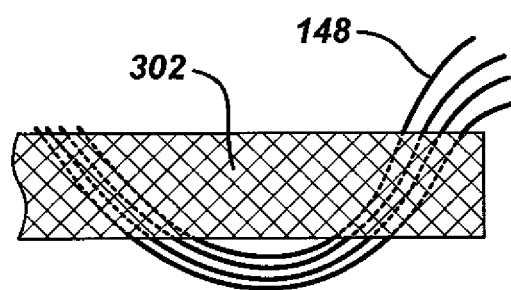
FIG. 20 is a side elevation view of an alternate usage of the suture threader of FIG. 19.

Alternatively, as shown in FIG. 20, the sutures 148 can be merely stitched through the braided tube 302. If the weave is open enough they can be stitched by hand or they can be stitched with needles (not shown). The tube 302 is then drawn through the cannulation 150 as in FIG. 19.

Figure 21:
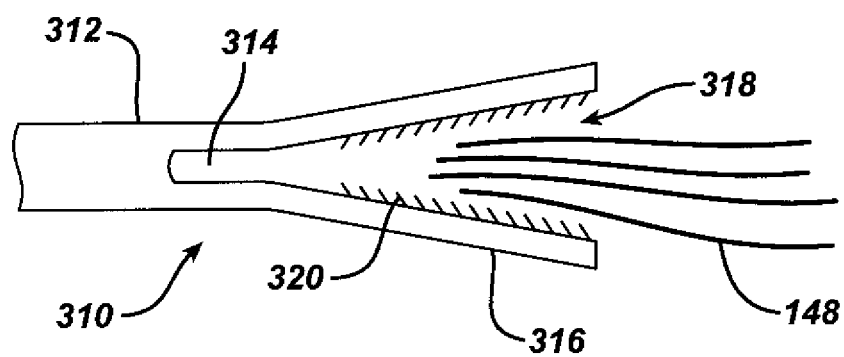
FIG. 21 is a side elevation view of a further embodiment of a suture threader according to the present invention.
Figure 22A:
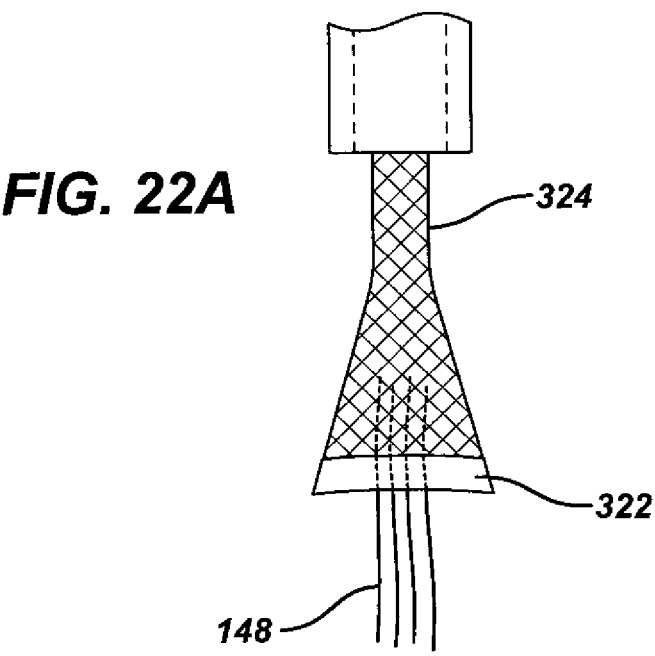
FIG. 22 A to D illustrate a further embodiment of a suture threader according to the present invention.
Figure 22B:
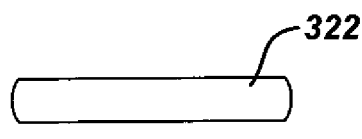
Figure 22C:
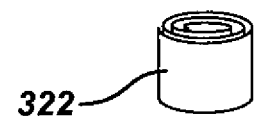
Figure 22D:
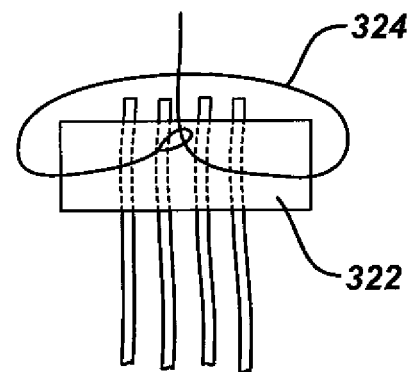

As shown in FIG. 21, a threader 310 can be formed from a tube 312 which is not necessarily braided but rather provided with axial slits 314 at one end 316 to form a mouth 318 for receiving the suture 148. Gripping enhancements such as teeth 320 can be provided within the mouth 318 to help retain the suture 148 therein as the threader 310 passes through the cannulation 150.

To ensure good closure of the expanded end 306 of the threader 300 of FIG. 19 it can be modified with additional closures as shown in FIGS. 22 A through D. For instance a simple spring metal snap element 322 can be provided to a braided tube 324, the element 322 having a first open position as shown in FIG. 22B and a second relaxed closed position as shown in FIG. 22C. After insertion of the sutures 148 with the element 322 in the open position is squeezed to pop it into the closed position. A loading suture loop 324 can be employed about the element 322 to provide the squeezing force for closure and also to further compress the sutures 148 within the tube 324. A separate loading suture loop 324 can also be provided alone and woven through the braid of the tube 324 in substitution of the element 322.

Figure 23A:
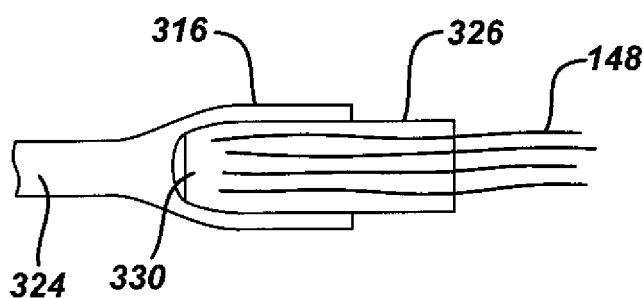
FIG. 23A is a top plan view of a further embodiment of a suture threader according to the present invention showing the braided tube in partial cut-away.
Figure 23B:
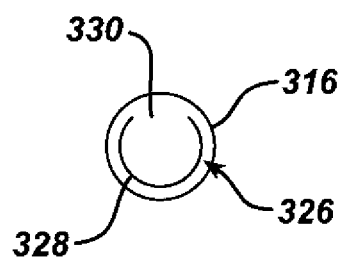
FIG. 23B is an end view of the suture threader of FIG. 23A.

Alternatively, the braiding of the tube 324 can be woven to encourage closure, especially if the material is resilient, and to hold the expanded end 316 open a stretcher 326 can be inserted therein as shown in FIGS. 23 A and B. In its simplest form the stretcher 326 comprises a tube 328 having a full length side opening 330 whereby after the suture 148 is loaded into the expanded end 316 the tube 328 is removed therefrom with the suture 148 passing through the opening 330 to allow removal of the tube 328.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method for affixing tissue to bone comprising the steps of:
    passing a length of suture through the tissue;
    passing the length of suture through a suture anchor, which comprises a tubular body having an axial bore therethrough, one or more purchase enhancements on an exterior surface of the body adapted to enhance purchase of the body within a bone hole, a lateral port through the body from the exterior surface into the axial bore, and a distal nose, the suture passing in order: distally down along the exterior surface over the one or more purchase enhancements, over the distal nose, up into the bore, proximally up through the axial bore, out through the lateral port, and proximally along the exterior surface over the one or more purchase enhancements;
    embedding the remainder of the suture anchor into the bone adjacent to the tissue and trapping the suture between the suture anchor body and the bone; and
    wherein upon application of an excessive force to the suture, the suture slips with respect to the anchor without anchor evulsion from the bone hole.

2. A method according to claim 1 wherein the purchase enhancements comprise at least one screw thread and wherein the step of embedding the suture anchor into the bone comprises threading the suture anchor into the bone hole.

3. A method according to claim 1 wherein the step of embedding the suture anchor into the bone is performed while maintaining an essentially fixed length of the suture between the bone hole and the tissue.

4. A method according to claim 1 wherein the bone hole has a diameter less than a diameter of the distal nose.

5. A method according to claim 4 wherein the bone hole diameter is at least 10 percent less than the diameter of the distal nose.

6. A method according to claim 1 wherein a longitudinal location of the lateral port on the anchor body between a distal end of the body and a proximal end of the body is selected to provide slippage of the suture with respect to the anchor without evulsion of the anchor from the bone hole.

* * * * *